US00PP37735P2

(12) United States Plant Patent
Southwick

(10) Patent No.: US PP37,735 P2
(45) Date of Patent: Oct. 6, 2026

(54) CHERRY TREE NAMED 'SMS-CA-05-RVT1191'

(50) Latin Name: ***Prunus avium* L.**
Varietal Denomination: SMS-CA-05-RVT1191

(71) Applicant: SMS UNLIMITED, LLC, Pensacola, FL (US)

(72) Inventor: Stephen M. Southwick, Pensacola, FL (US)

(73) Assignee: SMS UNLIMITED, LLC, Pensacola, FL (US)

( * ) Notice: Subject to any disclaimer, the term of this patent is extended or adjusted under 35 U.S.C. 154(b) by 0 days.

(21) Appl. No.: 19/433,671

(22) Filed: Dec. 26, 2025

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./180, 181, 183
See application file for complete search history.

(56) References Cited

U.S. PATENT DOCUMENTS

| | | | | |
|---|---|---|---|---|
| PP6,407 | P | 11/1988 | Bradford | |
| PP6,676 | P | 3/1989 | Hansche | |
| PP19,920 | P2 | 4/2009 | Zaiger | |
| PP22,779 | P3 * | 6/2012 | Zaiger | A01H 6/7445 Plt./181 |
| PP29,048 | P3 | 3/2018 | Southwick | |
| PP29,049 | P3 | 3/2018 | Southwick | |
| PP32,755 | P2 | 1/2021 | Southwick | |

* cited by examiner

*Primary Examiner* — Susan Mccormick Ewoldt
(74) *Attorney, Agent, or Firm* — Randall Danskin P.S.

(57) ABSTRACT

A new and distinct variety of sweet cherry tree, which is denominated varietally as 'SMS-CA-05-RVT1191' is described, with self-fertility and high productivity and which produces early ripening fruit considered large in size, with comparatively higher degrees Brix, and low in off-grade fruit types of deep suture, spurs, and doubled fruit formations under the ecological conditions prevailing in the Stockton and Lodi, California area.

5 Drawing Sheets

Latin name: *Prunus avium* L.

Variety denomination: The invention relates to a new, novel, and distinct variety of cherry tree, a *Prunus avium* L., with a variety denomination hereinafter as 'SMS-CA-05-RVT1191'.

SUMMARY

The variety is a new and distinct sweet cherry tree (*Prunus avium* L.) that is characterized by uniform cordate shaped fruit maturing 3-7 days after 'Royal Tioga' (U.S. Plant Pat. No. 22,779) in Stockton and Lodi, California area. Fruit production is high with self-fertility, while at the same time fruit size is large with some reaching 34 millimeters (mm) and the average 29 mm. The stem is long and strongly attached. The production of off-grade fruit types, such as deep suture, spurs, and doubled fruit, is lower and the degrees Brix (° Bx) levels are higher than comparative varieties ripening in the early period. The fruit has a glossy, shiny finish. It is firm with exceptional taste and consumer appeal. The fruit maturity is uniquely early with exceptional productivity, fruit size and taste characteristics differing from cultivars compared. The variety appears to have good shipping quality for an early season variety, although shipping trials have been limited. The flowering period and compatibility is matched with the 'SMS-CA-05-1190' variety (U.S. patent application Ser. No. 19/433,667), which has a seed parent in common, and 'SMS-CA-05-1191' is a suggested pollinator.

ORIGIN

The variety was discovered from an open pollination of seeds collected from a proprietary sweet cherry selection SC3-36 where individual trees of SC3-36 were located near Vina and Lodi, California in 1999. The trees were in blocks with others of the breeder's selections including SC3-13 (unpatented), SC3-35 (unpatented), SC3-36a (unpatented), 'SMS-1-CA-WA 2014-1' (U.S. Plant Pat. No. 32,755), 'SMS-9CA 2014-9' (U.S. Plant Pat. No. 29,049), 'SMS-16-CA 2014-16' (U.S. Plant Pat. No. 29,048), and other commercial varieties, including 'Coral' (syn. 'Coral Champagne', unpatented), 'Brooks' (U.S. Plant Pat. No. 6,676), 'Tulare' (U.S. Plant Pat. No. 6,407) and neighboring orchards in the Vina and Lodi areas.

The seed parent 'SC3-36' fruiting characteristics include early ripening fruit in late April ahead of or with 'Royal Tioga' with similar or larger fruit size and moderate crop production. In addition, the fruit had off-grade types, generally referred to as deep suture, spurs, and doubled fruit, ranging from 7 to 30%. Moreover, 'SC3-36' had Brix levels around 16°.

ASEXUAL REPRODUCTION

The seeds were stratified, testa removed, and germinated and planted in pots in 2000. After germination, they were grown in pots for 4 years until flowering. Fruit were first observed in 2004. Buds were taken in that same year and propagated on *Prunus mahaleb* rootstock for further evaluation in Vina and Stockton, California in 2004. Additional trials were conducted in Lodi, Kingsburg, and Bakersfield, California. In 2008, the first fruit were evaluated in the Stockton area. Additional observations after further propagation on *Prunus mahaleb* rootstock in 2014 have been ongoing primarily in the Stockton-Lodi area of California until 2025.

Throughout the aforementioned trials and various asexual propagations, the tree and fruit produced thereby were compared to the originally discovered plant. All characteristics of the original tree and its fruit were established and appears to have been transmitted to the aforementioned succeeding generations.

COMPARISONS

The variety 'SMS-CA-05-RVT1191' is an open pollinated early ripening sweet cherry selection maturing 3-7 days after 'Royal Tioga' and 4-8 days before 'Brooks' and 'Coral' in the Stockton-Lodi region of California. 'SMS-CA-05-RVT1191' is distinct from other sweet cherry selections because it is early maturing, has a long strongly attached stem to the fruit, is productive, has large size, has a lower production of fruit with deep suture, spurred and doubled fruit and is firm with a distinctive shine and outstanding organoleptic qualities. The variety is consistently productive and has a low percentage of fruit with a depressed suture line (deep suture). It can crack with rain, but is considered to be moderate and consistent with other commercial varieties like 'Coral'. Table 1 below summarizes comparisons to 'Royal Tioga' and 'Royal Hazel' (U.S. Plant Pat. No. 19,920).

TABLE 1

Royal Tioga, Royal Hazel and SMS-CA-05-RVT1191 fruiting characteristics in the Stockton-Lodi region of California from seasons 2016, 2017, 2018, 2021, and 2023.

| | Variety/Selection | | |
|---|---|---|---|
| Fruiting characteristics | 'Royal Tioga' | 'Royal Hazel' | 'SMS-CA-05-RVT1191' |
| Fruit production/tree Rating (1-5[1]) | 4-5 | 2-4 | 3-4 |
| Fruit size (mm/fruit) | 25-29 | 25-28 | 26-33 |
| °Brix | 14-18 | 15-18 | 16-22 |
| Variance of initial harvest date; standard conditions | April 28 to May 5 | May 9 to May 19 | May 2 or 3 to May 12 |
| Fruit with suture, spur, and double (%) | 10-65 | 5-40 | 2-20 |

[1]Rating 1 = Low 0-5 kg/tree, 2 = 5-10 kg/tree, 3 = 10-25 kg/tree, 4 = 25-50 kg/tree, 5 = 50+ kg/tree.

Table 1 indicates fruit production per tree is less for 'SMS-CA-05-RVT1191' compared to 'Royal Tioga'. Initially, the fruit production of 'SMS-CA-05-RVT1191' may appear less desirable. Fruit production varies somewhat by year for both varieties. When 'Royal Tioga' fruit production is very high, which occurs quite often, it yields small fruit. An attempt may be made to increase fruit size by hand thinning, increasing production cost, but it is not always successful. Since the market evolved to accept small fruit no longer, the very high fruit production of 'Royal Tioga' is less desirable than it may seem. With its somewhat lower fruit production, 'SMS-CA-05-RVT1191' is a more desirable variety because, even during a high production year, trees yield fruit of marketable size without the extra cost and unreliable results of thinning. Thus, 'SMS-CA-05-RVT1191' is a high producer, but not an over producer. In the current market environment and for the foreseeable future, it is more economically favorable to have a somewhat lower yield per tree than a very high one.

Figure 1:
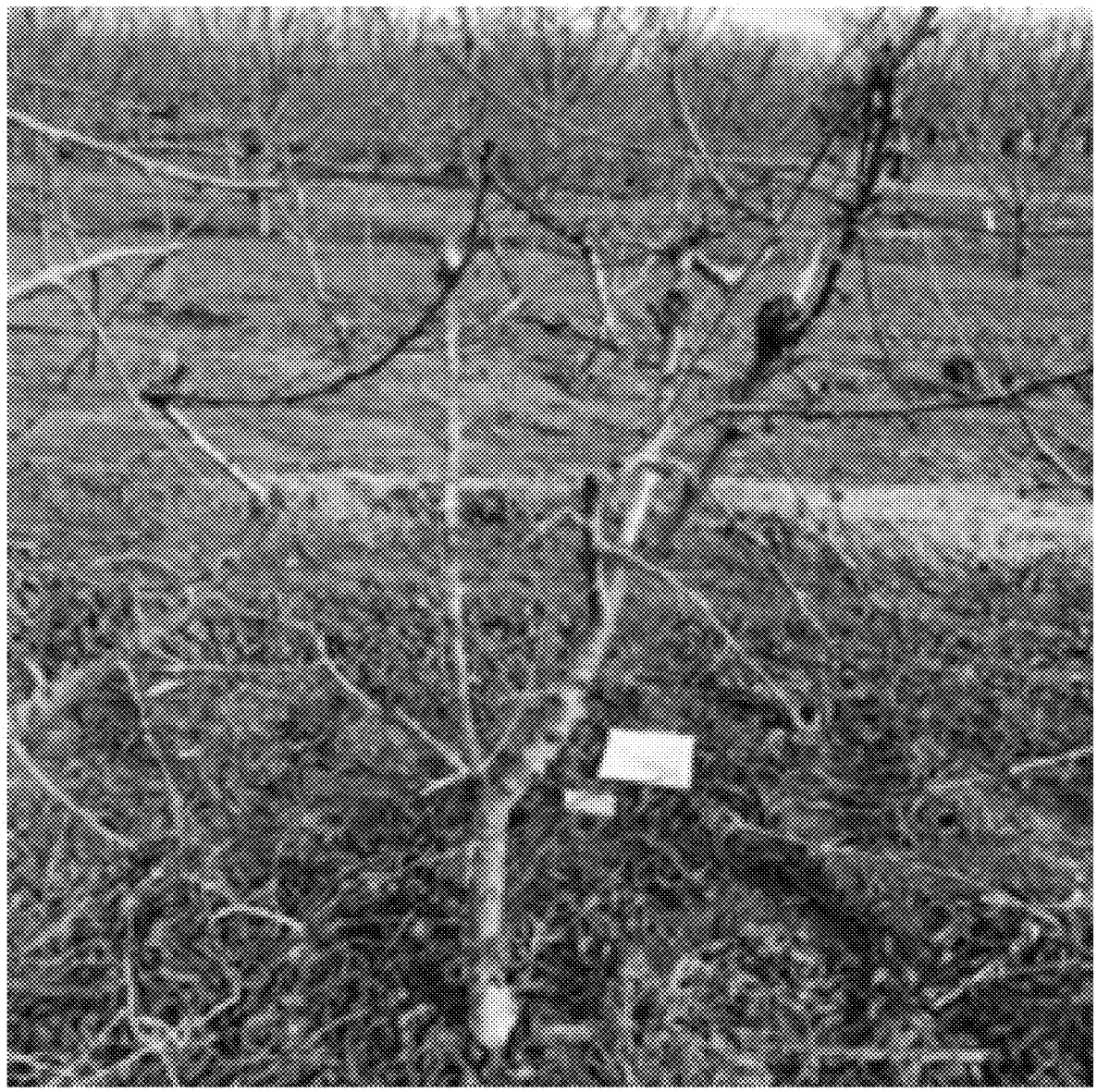
FIG. 1 is a color photograph showing the dormant 'SMS-CA-05-RVT1191' mother tree.
Figure 2:
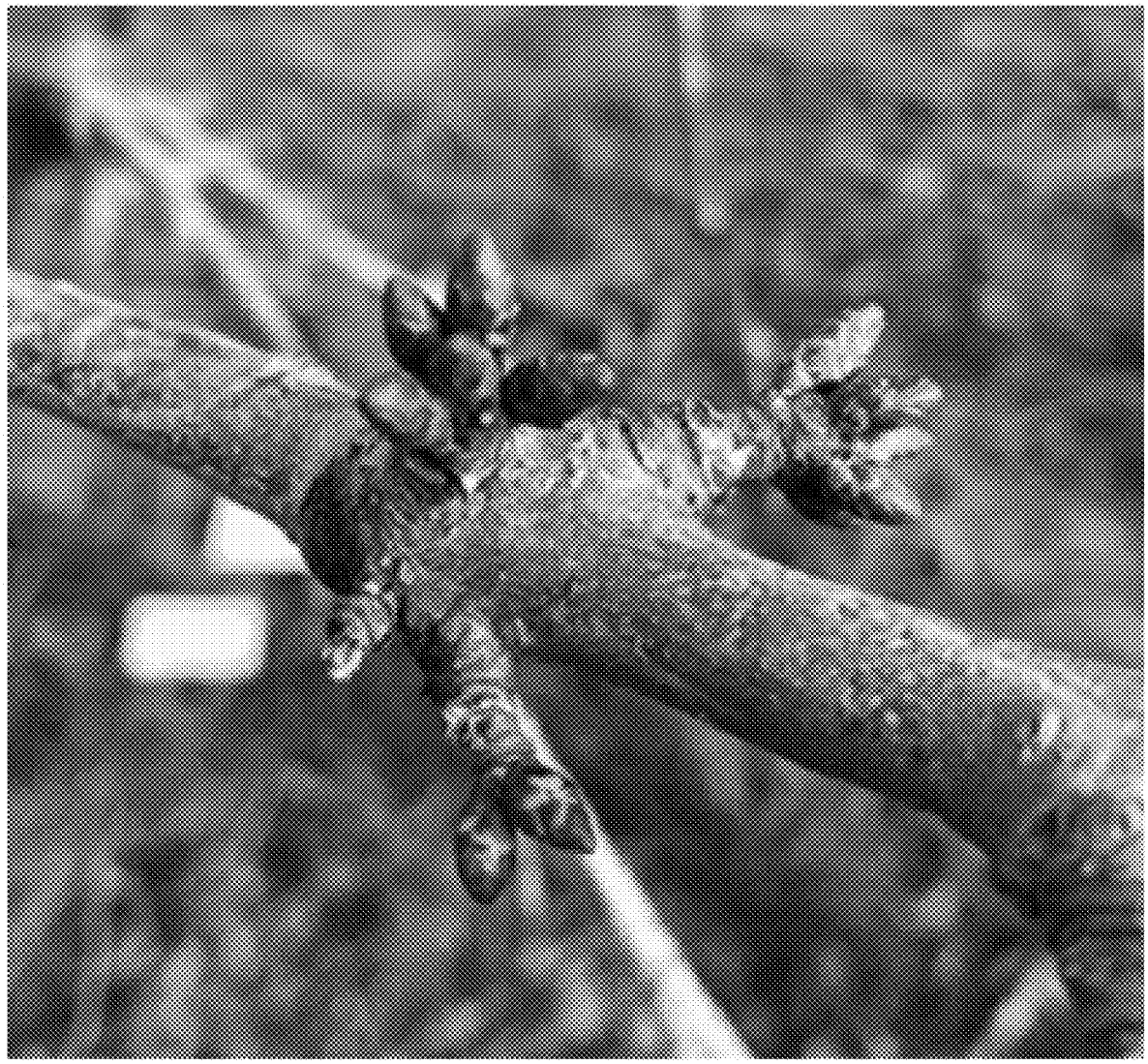
FIG. 2 is a color photograph showing dormant fruiting bud development of the 'SMS-CA-05-RVT1191' mother tree.
Figure 3:
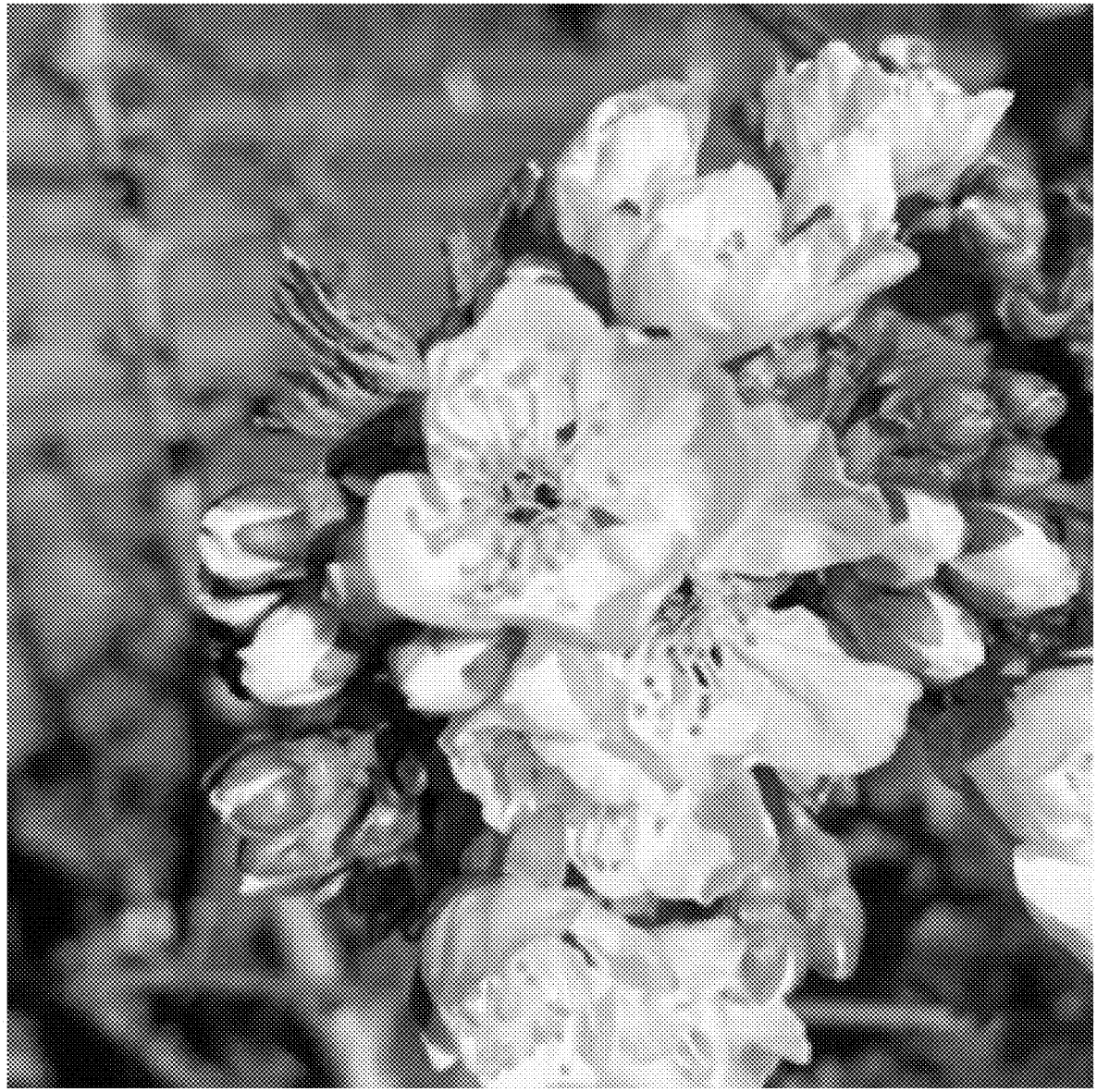
FIG. 3 is a color photograph showing blossoms of the 'SMS-CA-05-RVT1191' mother tree near full bloom.
Figure 4:
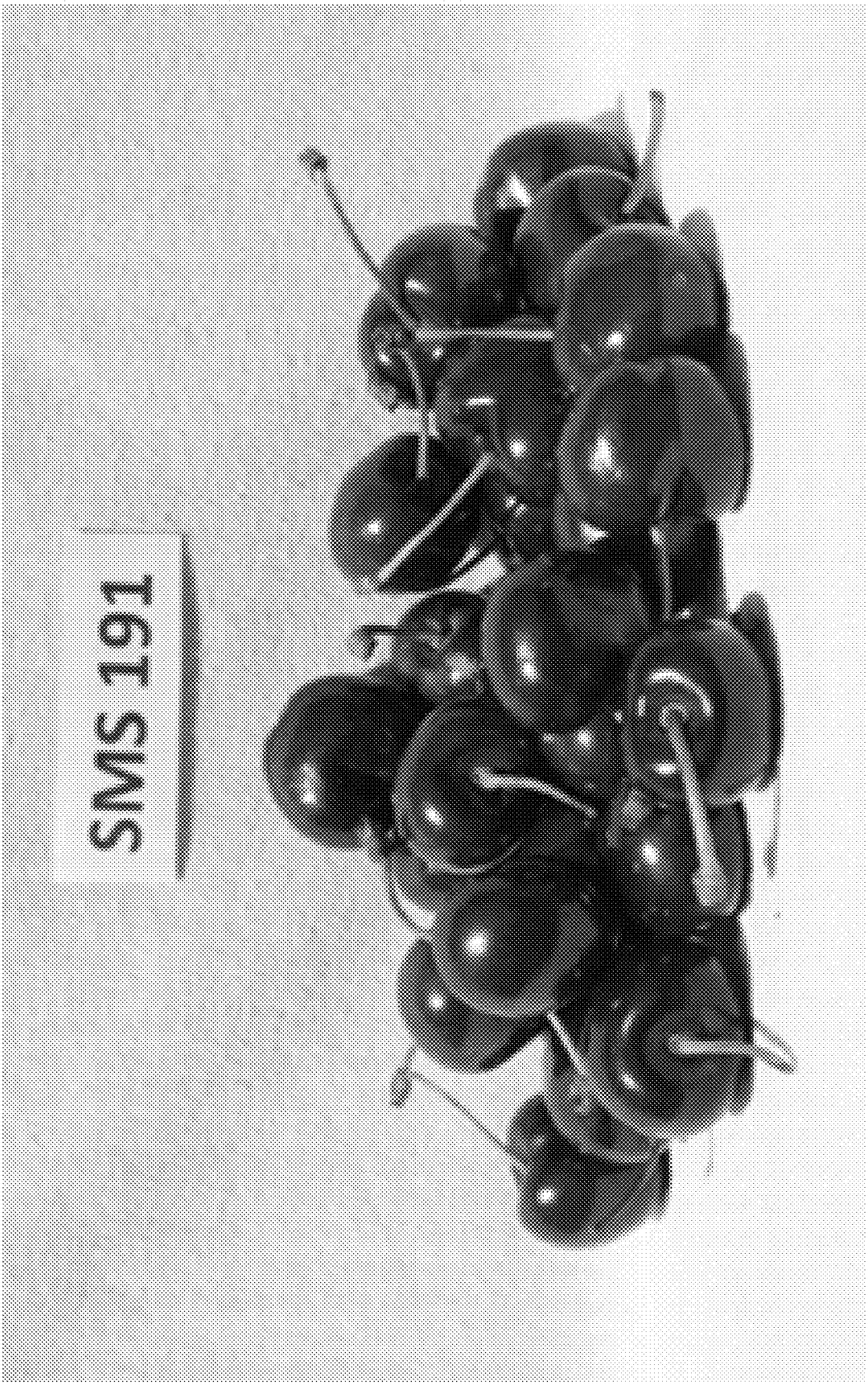
FIG. 4 is a color photograph showing the 'SMS-CA-05-RVT1191' fruit at harvest maturity.
Figure 5:
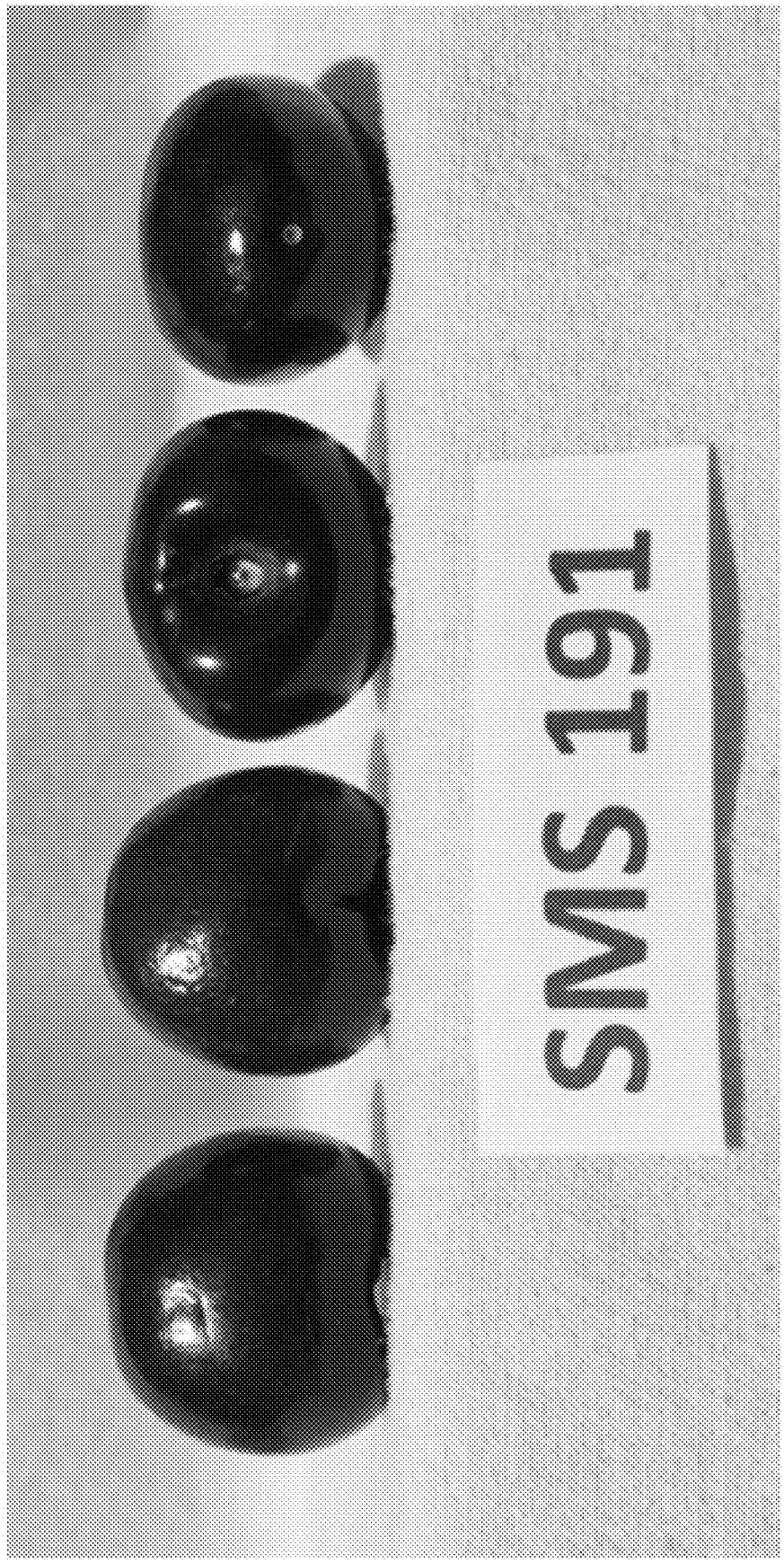
FIG. 5 is a color photograph showing (left to right) the front, back, top, and bottom of mature 'SMS-CA-05-RVT1191' fruit.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Fourth Edition, 2001, hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of cherry tree, the following has been observed from the 10-year-old 'mother' tree under the ecological conditions prevailing at the breeder's property, which is located near Lodi, California.

Tree:

*Height.*—7 feet, 6 inches.

*Diameter.*—6 feet, 2 inches at time of description.

*Vigor.*—Considered moderate.

*Branching habit.*—Considered moderate.

*Density.*—Considered moderately dense.

*Form.*—Considered open vase.

*Hardiness.*—Considered hardy for Stockton-Lodi region of California.

*Production.*—Precocity — Yes, some fruit in year 3, common by year 4. Yield per acre — Varies with the season, 6 to 8.5 tons per acre favored.

*Bearing.*—Annual.

Trunk:

*Size.*—32 centimeters (cm) circumference at 30 cm above ground.

*Bark texture.*—Smooth.

*Bark color.*—RHS Greyed-Green Group 188A.

*Lenticels*.—Prominence — Prominent with a horizontal orientation. Length — Ranges from 3.0 mm to 6.0 mm with an average of 3.9 mm. Width — Ranges from 0.4 mm to 1.0 mm with an average of 0.7 mm. Number — 12 per 9 $cm^2$. Color — RHS Brown Group 200B.

Branches:

*Scaffold branches*.—Bark Texture — Smooth. Size — Circumference at 10 cm from trunk union ranges from 15.2 cm to 10.7 cm with an average of 13.0 cm. Angles as trained range from 55 to 65 degrees from horizontal. Color — RHS Greyed-Orange Group 176A. Lenticels — Generally numerous and variable, averaging 6.2 per 9 $cm^2$. Length ranges from 1.35 mm to 3.6 mm with an average of 2.6 mm. Width consistent at 1.0 mm. Center color is RHS Greyed-Orange Group 172B. Outer margin color is RHS Greyed-Green Group 198D.

*Second-year fruiting branches*.—Texture — Smooth. Diameter — Averages 6.0 mm at mid-point of growth. Color — RHS Greyed-Orange Group 177A. Lenticels — 8 per running cm. Round in shape. Color is 165B.

*Current-year branches*.—Texture — Smooth. Size — Length ranges from 10 cm to 90 cm with an average of 50 cm. Diameter ranges from 5.0 mm to 6.0 mm with an average of 5.5 mm. Color — RHS Greyed-Orange Group N170A. Internode length — 16 mm to 46 mm with an average of 30 mm. Lenticels — 12 per running cm. Round shape. Size ranging from 0.15 mm to 0.4 mm with an average of 0.285 mm. Color is RHS Greyed-Yellow Group 161D.

Dormant flower buds: (as measured at full bud swell).

*Spur length*.—Ranges from 4.2 mm to 6.5 mm with an average of 5.9 mm.

*Bud shape*.—Ovoid.

*Number of buds per fruiting spur*.—Ranges from 7 to 9, mostly 7.

*Bud length*.—Ranges from 6.1 mm to 9.1 mm with an average of 8.4 mm.

*Bud diameter*.—Ranges from 3.5 mm to 4.0 mm with an average of 3.7 mm.

*Scale color*.—RHS Greyed-Red Group 178A.

Leaves: (as measured from midpoint of actively growing current season's growth at harvest maturity).

*Texture*.—Upper surface is smooth and leathery, lower surface is smooth with vein protruding 0.3 mm to 1.1 below surface.

*Form/shape*.—Narrow acute (lanceolate).

*Tip shape*.—Acuminate.

*Base*.—Rounded.

*Blade size*.—Length — Ranges from 12.2 mm to 17.0 mm with an average of 13.8 mm. Width — Ranges from 4.5 mm to 8.0 mm with an average of 5.9 mm. Thickness — Ranges from 0.14 mm to 0.16 mm.

*Margin*.—Double-serrate.

*Midvein*.—Diameter ranges from 0.8 mm to 1.3 mm with an average of 1.1 mm. Color is RHS Yellow-Green Group 145D.

*Upper blade color*.—RHS Yellow-Green Group 147B.

*Lower blade color*.—RHS Yellow-Green Group 147B.

*Petiole*.—Length — Ranges from 3.5 cm to 4.3 cm with an average of 4.0 cm. Diameter at mid-point — Ranges from 1.3 mm to 1.9 mm with an average of 1.5 mm. Upper surface color — RHS Grey-Brown Group N199D. Lower surface color — RHS Yellow-Green Group 152A. Glands — Shape is mostly oval, some elliptic, with 2 in number, occasionally 5, on average 3. Opposite in position when only 2, alternate in position when only 3 or more. Located 0.1 mm to 7.2 mm from blade. Length ranges from 1.6 mm to 2.3 mm. Width ranges from 1.0 mm to 2.0 mm. Color is RHS Grey-Red Group 182A. Stipules — None.

*Attitude*.—Moderate droop.

Flowers:

*Attitude*.—Bloom stands out with moderate droop.

*First bloom*.—March 11 under the ecological conditions prevailing in Lodi, California. Three-year average is March 15.

*Size*.—Considered medium. Bloom diameter when fully open ranges from 27.2 mm to 45.5 mm with an average of 30.4 mm.

*Bloom count per bud*.—A nearly consistent 3 with an occasional 2.

*Petals*.—Number — Five. Shape — More obovate than round. Length — Ranges from 12.0 mm to 14.5 mm with an average of 13.4 mm. Width — Ranges from 11.9 mm to 15.8 mm with an average of 13.9 mm. Base — Rounded. Apex — Considered emarginate. Color — RHS White Group 155D. Touch — When fully open, petals touch.

*Stamens*.—Filament — Thirty. Length ranges from 4.2 mm to 10.5 mm with an average of 7.8 mm. Color of upper ⅔ is RHS White Group 155D and basal ⅓ is RHS White Group N155D. Anther — Shape is globose. Length is 1.2 mm. Width is 1.0 mm. Pollen is considered abundant with color in RHS Greyed-Yellow Group 161A.

*Carpel*.—Style — Length ranges from 8.7 mm to 11.4 mm with an average of 10.1 mm. Diameter at mid-point ranges from 0.3 mm to 0.5 mm with an average of 0.4 mm. Color is RHS Yellow-Green Group 145A. Stigma — Not clubbed, round in shape with flat top. Diameter ranges from 0.5 mm to 0.7 mm. Color is RHS Grey-Brown Group 199D. Nectary color — RHS Yellow-Green Group 146B.

*Sepals*.—Number — Five. Shape — Elliptical. Orientation over thalamus — Laid back and touching. Length — Ranges from 5.2 mm to 6.3 mm with an average of 5.6 mm. Width — Ranges from 2.9 mm to 4.2 mm with an average of 3.4 mm. Color — Inner is RHS Green Group N138A. Outer surface is RHS Greyed-Purple Group 187A.

*Peduncle*.—Length — Ranges from 9.5 mm to 16.8 mm with an average of 13.0 mm. Diameter at mid-length — Ranges from 0.7 mm to 1.0 mm with an average of 0.9 mm. Color — RHS Green Group 138A.

*Thalamus*.—Shape — Urn. Depth — Ranges from 5.1 mm to 6.8 mm with an average of 6.1 mm. Width — Ranges from 3.7 mm to 5.3 mm with an average of 4.3 mm. Color — RHS Yellow-Green Group 144A.

Fruit:

*Maturity*.—Considered uniform. Harvest date varies May 2 or 3 to May 12 under the ecological conditions prevailing in Lodi, California.

*Quantity per cluster*.—1 to 2, mostly 1.

*Form*.—Uniformity — Uniform. Considered more round heart-shaped than cordate with backside flattened. Base shape — Round with russet dot in center that is 0.5 mm below surface and 2.0 mm in diameter. Dot color is RHS Greyed-Orange Group 164D. Apex Shape — Considered round. Depression width ranges from 10.0 mm to 12.4 mm with an average of 11.7 mm. Depression depth ranges from 3.8 mm to 5.5 mm with an average of 5.0 mm. Not russetted.

*Size*.—Apical diameter — Ranges from 22.6 mm to 25.8 mm with an average of 24.2 mm. Axial side to side diameter — Ranges from 25.6 mm to 28.1 mm with an average of 26.9 mm. Suture axial diameter — Ranges from 21.0 mm to 23.1 mm with an average of 21.9 mm.

*Suture*.—Faintly distinct to non-distinct on 50% of fruit, width 0.8 mm to 1.0 mm, depth is flush where present on backside of fruit.

*Peduncle*.—Length — Ranges from 23.3 mm to 31.5 mm with an average of 27.1 mm. Diameter at mid-point — Ranges from 1.0 mm to 1.3 mm with an average of 1.1 mm. Color — RHS Yellow-Green Group 146B.

*Skin*.—Thickness — 0.05 mm to 0.06 mm. Texture — Smooth. Tenacity — Moderately light, easily tears when peeled. Tendency to crack — Occasional light cracking observed at stem end on 10% of fruit. Down — None. Color — RHS Greyed-Purple Group 187A.

*Flesh*.—Color — RHS Greyed-Purple Group 183A. Surface of pit cavity color — RHS Greyed-Purple Group 187A. Texture — Smooth. Fibers — None observed. Pit tenacity — Moderately light. Ripens — Evenly. Flavor — Cherry-like with moderate intensity. Aroma — Lacking. Eating quality — Excellent, very firm and sweet with low acid.

*Stone*.—Type — light cling type. Size — Base to apex ranges from 10.1 to 11.9 mm with an average of 11.0 mm. Shoulder to shoulder ranges from 7.0 to 8.0 mm with an average of 7.5 mm. Suture to suture ranges from 8.4 mm to 9.1 mm with an average of 8.8 mm. Form — Considered elliptic. Base — Rounded. Apex — Mostly mucronate, some rounded. Sides — Equal (uniform). Surface — Smooth. Ventral Edge — Suture from base to apex is slightly raised 0.1 to 0.2 mm and is subtended by two low ridges converging basally and apically that averages 0.2 to 0.7 mm in height at the mid-point and range from 4.0 to 4.7 mm apart at the midpoint. Dorsal Edge — Suture is raised 0.1 to 0.2 mm. Color — RHS Greyed-Orange Group 164A. Tendency to split — None observed, but consistent or less compared with other commercial varieties with similar ripening time.

*Kernel*.—Shape — Considered narrow acute. Rounded base. Acute apex. Size — Length ranges from 6.9 mm to 8.5 mm with an average of 7.6 mm. Width ranges from 3.9 mm to 4.5 mm with an average of 4.2 mm. Thickness ranges from 1.5 mm to 3.6 mm with an average of 3.0 mm. Color — RHS Greyed-Orange Group 164B. Taste — Bitter almond-like. Viability — 100% kernel development observed, viable kernel germination unknown.

*Pollination requirement*.—Self-fertile (alleles S4' S9).

*Use*.—Fresh.

*Keeping quality*.—Fruit firmness Durofel 85. From 2-4 weeks at 32° F.

*Resistance to insects and diseases*.—Considered standard with other commercial sweet cherry varieties of the Stockton-Lodi region of California.

*Shipping quality*.—Very good for commercial quality based on limited testing.

Although the new variety of cherry tree possesses the described characteristics when grown under the ecological conditions prevailing in Stockton and Lodi, California, it should be understood that variations are to be expected in the usual magnitude and characteristics incident to changes in growing conditions, fertilization, pruning, pest control, frost, climatic variables, and horticultural management.

The invention claimed is:

1. A new and distinct variety of sweet cherry tree, substantially as illustrated and described, which is characterized principally as to novelty by self-fertility, by high productivity, and by producing early ripening fruit considered large in size, with comparatively higher degrees Brix, and low in off-grade fruit types of deep suture, spurs, and doubled fruit formations under the ecological conditions prevailing in the Stockton and Lodi, California area.

* * * * *